United States Patent

Satomi et al.

[11] 3,943,203
[45] Mar. 9, 1976

[54] PHOSPHOROTHIONOAMIDATES

[75] Inventors: Takeo Satomi, Takarazuka; Kunio Mukai, Nishinomiya; Akihiko Mine; Naganori Hino, both of Toyonaka; Kohshi Tateishi, Minoo, all of Japan

[73] Assignee: Sumitomo Chemical Company, Limited, Japan

[22] Filed: Oct. 5, 1971

[21] Appl. No.: 186,760

[30] Foreign Application Priority Data
Dec. 25, 1970  Japan............................. 45-129021

[52] U.S. Cl................................. 260/954; 71/87
[51] Int. Cl.² .................................... C07F 9/24
[58] Field of Search............................ 260/954, 959

[56] References Cited
UNITED STATES PATENTS

| 3,107,164 | 10/1963 | Szabo et al. | 260/954 X |
| 3,231,359 | 1/1966 | Newallis et al. | 260/954 X |
| 3,636,143 | 1/1972 | Schrader | 260/954 |
| 3,787,538 | 1/1974 | Schrader et al. | 260/954 |

Primary Examiner—Richard L. Raymond
Attorney, Agent, or Firm—Wenderoth, Lind & Ponack

[57] ABSTRACT

A phosphorothionoamidate of the formula,

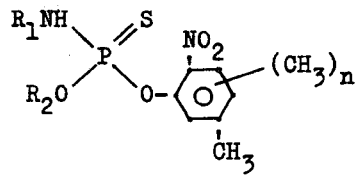

wherein $R_1$ is a $C_3 - C_4$ alkyl, $R_2$ is a $C_1 - C_4$ alkyl, and $n$ is an integer of 1 to 3, which is useful as a herbicide.

7 Claims, No Drawings

PHOSPHOROTHIONOAMIDATES

The present invention relates to a novel phosphorothionoamidate represented by the formula,

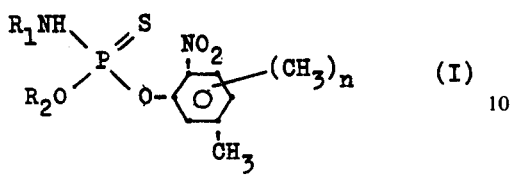

wherein $R_1$ stands for an alkyl group having 3 or 4 carbon atoms, $R_2$ stands for an alkyl group having 1 to 4 carbon atoms, and $n$ stands for an integer from 1 to 3, and herbicidal compositions containing the same.

The present herbicidal compositions are useful for controlling weeds both in upland and paddy fields, such as grass family weeds, for example barnyard grass, large crab grass, water foxtail, etc. and broad-leaved weeds, for example redroot pigweed, common lambsquater, monochoria, slender spikerush, etc.

The compounds of this invention may be synthetized by reacting a thionophosphoric chloride of the formula,

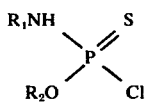

wherein $R_1$ and $R_2$ are as mentioned above with a nitrophenol represented by the formula,

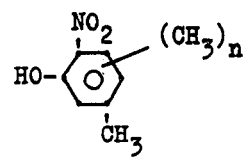

wherein $n$ is as mentioned above in an organic solvent in the presence of an acid binding agent.

Examples of the solvents used in this invention include aromatic solvents such as benzene and toluene, and ketones such as acetone and methyl isobutyl ketone, and acetonitrile, etc.

Examples of the acid binding agents include inorganic bases such as potassium carbonate and sodium hydroxide, tertiary amines such as pyridine and triethylamine, and a mixture thereof.

The reaction temperature varies depending on the kind of the solvent or acid binding agent to be used. The reaction is preferably carried out at a temperature of from room temperature to about 120°C. for 2 to several hours.

Examples of the compounds synthetized by the above method are as follows, but the present invention is not limited to these compounds.

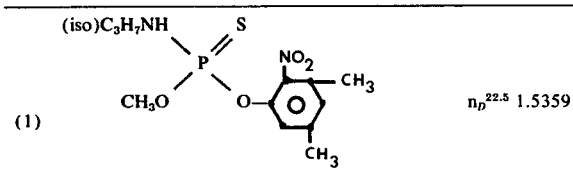

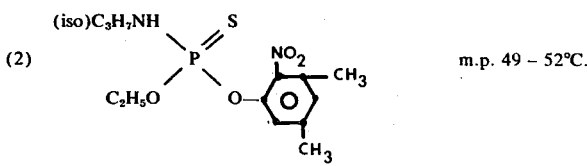

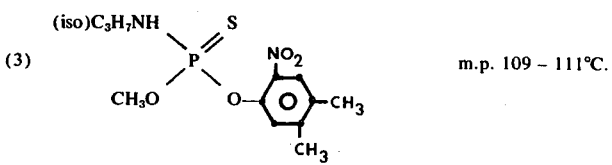

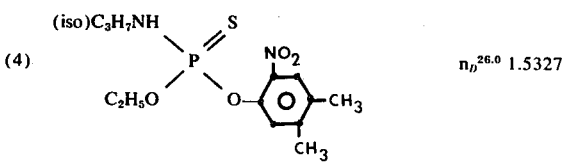

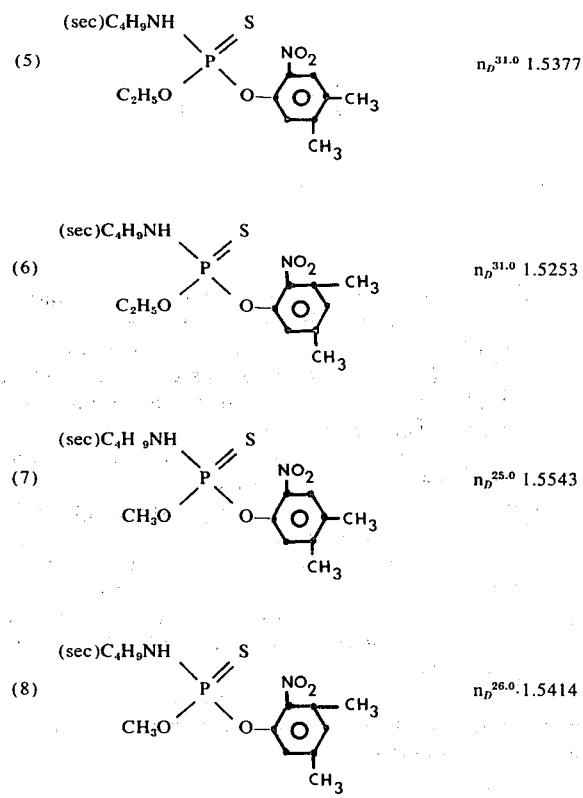

Compounds having similar structure to that of the compounds of this invention are found in U.S. Pat. No. 2,552,576. However they are different from the compounds of this invention in that they have only nitro group or other groups as the substituents for the phenyl group and their use is directed to insecticides and fungicides.

Further, Dutch Patent Nos. 6,916,095 and 6,916,096, U.S. Pat. No. 3,074,790 and Belgian Pat. No. 745,633 describe herbicidal action of compounds having structure resembling that of the compounds of this invention. However, the compounds of this invention are different in structure from the said compounds, and are superior in herbicidal effects to said compounds, as is substantiated in the Test Examples mentioned below.

The present inventors have discovered the excellent herbicidal activity of the compounds of this invention for which 2-nitro and 5-methyl groups on the benzene ring are essential.

The herbicidal characteristics of the compounds of the present invention are described in the following:

When subjected to pre-emergence treatment of weeds, the compounds display strong herbicidal activities against a wide scope of weeds such as, for example, barnyard grass (*Eleocharis crus-galli*), slender spike-rush (*eleocharis acicularis*), monochoria (*Monochoria viaginalis Presl.*), false pimpernel (*Linderna pyxidaria*), toothcup (*Rotala indica Koehne*), etc. More surprisingly, the compounds can successfully control the aforesaid weeds without any phytotoxicity to transplanted rice seedings. Therefore, the present compounds are quite excellent as herbicides for paddy rice fields. Further, when applied to upland fields, the present compounds have strong herbicidal activities on many weeds, e.g. grass family weeds such as barnyard grass (*Echnochloa crus-galli*), large crabgrass (*Digitaria sanguinalis*), green foxtail (*Setaria viridis*) and water foxtail (*Alopecurus aequalis*), and such broad-leaved weeds as common purslane (*Portulaca oleracea*), redroot pigweed (*Amaranthus retroflexus*), common lambsquarter (*Chenopodium album*) and chickweed (*Stellaria media*), and can effectively control the aforesaid weeds without any phytotoxicity to crops such as, for example, rice, radish, soy bean, pea, carrot and cotton. Therefore the compounds may be applied to cereals, beans and vegetables, orchards, turfs, pasture lands and non-crop lands.

The present compounds are extremely low in toxicity to mammals and fishes.

In actual application, the compounds of the present invention may be used as they are or may be used in the form of any of such preparations as granules, dusts, wettable powders, emulsifiable concentrates, oil spray and aerosol. These preparations are desirably used so as to conform to the kinds and sizes of crops and to the purposes of application. In formulating the present compounds, there are used such solid carriers as, for example, talc, bentonite, clay, kaolin, diatomaceous earth, vermiculite and calcium hydroxide; and such liquid carriers as, for example, benzene, alcohols, acetone, xylene, dioxane, methyl naphthalene and cyclohexanone. In actual application, the present compounds may be enhanced and ensured in effectiveness by using them in admixture with surface active agents such as spreaders and stickers and the like. It is also possible to use the present compounds in admixtures with fungicides, insecticides, nematocides, other herbicides and similar agricultural chemicals and with fertilizers.

The present invention is illustrated in further detail below with reference to examples, which are only illustrative, but not limitative. All parts and percents are by weight.

EXAMPLE 1

To a solution of 16.7 g. of 3,5-dimethyl-6-nitro phenol dissolved in 150 ml. methylisobutylketone, 117 g. of anhydrous sodium carbonate was added at 60°C. and the mixture was stirred for 15 minutes at that temperature.

Then 18.8 g. of thionophosphoric acid o-methyl-N-isopropylamide chloride was added dropwise at 60° – 65°C. over a 30 minutes period. Thereafter, the mixture was refluxed under stirring for 4 hours.

After removal of the solvent under reduced pressure, the residue was mixed with benzene and washed with water repeatedly. The benzene was removed under reduced pressure to obtain a reddish brown, oily crude ester. This crude ester was further subjected to column chromatography with active alumina and benzene. As a pale yellow oil, 22.6 g. of o-methyl-o-(3,5-dimethyl-6-nitro phenyl-N-isopropyl thionophosphoric acid amidate, $n_D^{22.5}$ 1.5359 was obtained.

Elementary analysis:
(as $C_{12}H_{19}N_2O_4PS$)

|   | Calculated (%) | Found (%) |
|---|---|---|
| P | 9.73 | 9.60 |
| S | 10.07 | 10.21 |
| N | 8.80 | 8.62 |

EXAMPLES 2 TO 8

According to the procedure similar to that of Example 1, the following compounds were obtained.

| Example No. | $R_1$ | $R_2$ | structure | Acid binding reagent | Solvent used | Reaction time and temperature | Yield (%) | Physical constant | Elementary analysis Calculated (%) | Found (%) |
|---|---|---|---|---|---|---|---|---|---|---|
| 2 | (iso)$C_3H_7$ | $C_2H_5$ | 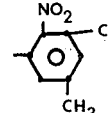 | $K_2CO_3$ | Acetonitrile | 4 hrs. 80°C. | 78 | m.p. 49–52°C. | P 9.32<br>S 9.65<br>N 8.43 | 9.15<br>9.84<br>8.01 |
| 3 | " | $CH_3$ | 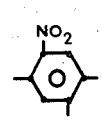 | " | " | " | 76 | m.p. 109–111°C. | P 9.73<br>S 10.07<br>N 8.80 | 9.67<br>10.23<br>8.54 |
| 4 | " | $C_2H_5$ | 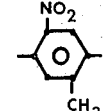 | Pyridine | " | 5 hrs. 80°C. | 73 | $n_D^{26.0}$ 1.5327 | P 9.32<br>S 9.65<br>N 8.43 | 9.49<br>9.43<br>8.26 |
| 5 | (sec)$C_4H_9$ | $CH_3$ | 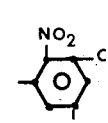 | $K_2CO_3$ | Toluene | " | 70 | $n_D^{26.0}$ 1.5414 | P 9.32<br>S 9.65<br>N 8.43 | 9.61<br>9.79<br>8.21 |
| 6 | (sec)$C_4H_9$ | $C_2H_5$ | 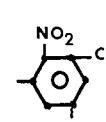 | $K_2CO_3$ | Toluene | 5 hrs. 80°C. | 71 | $n_D^{26.0}$ 1.5278 | P 8.94<br>S 9.25<br>N 8.09 | 8.66<br>9.57<br>7.97 |

| Example No. | $R_1$ | $R_2$ | (Ar group) | Acid binding reagent | Solvent used | Reaction time and temperature | Yield (%) | Physical constant | Elementary analysis Calculated (%) | Found (%) |
|---|---|---|---|---|---|---|---|---|---|---|
| 7 | " | $CH_3$ | 2-NO$_2$-4,6-di-CH$_3$-phenoxy | " | Acetonitrile | 4 hrs. 80°C. | 73 | $n_D^{25.0}$ 1.5543 | P 9.32 S 9.65 N 8.43 | 9.11 9.92 8.37 |
| 8 | " | $C_2H_5$ | 2-NO$_2$-4,6-di-CH$_3$-phenoxy | " | " | " | 75 | $n_D^{26.0}$ 1.5402 | P 8.94 S 9.25 N 8.09 | 8.78 9.41 7.97 |

EXAMPLE 9

Wettable powder:

25 Parts of the compound (6), 5 parts of a surface active agent of the polyoxyethylene acetylallylester type and 70 parts of talc were thoroughly pulverized and mixed together to obtain a wettable powder.

EXAMPLE 10

Emulsifiable concentrate:

30 Parts of the compound (2), 20 parts of an emulsifier of the polyethylene glycol ether type and 50 parts of cyclohexanone were thoroughly mixed together to obtain an emulsifiable concentrate.

EXAMPLE 11

Granule:

8 Parts of the compound (4), 38 parts of bentonite, 50 parts of clay and 4 parts of sodium lignosulfonate were thoroughly pulverized and mixed together. The resulting mixture was sufficiently kneaded with water, and then granulated and dried to obtain granules.

In order to substantiate the prominent effects of the present compounds as herbicides, detailed illustration is given below with reference to typical test examples, in which the names of the compounds are represented by the numbers of the previously exemplified compounds.

TEST EXAMPLE 1

Pre-emergence application:

Seeds of barnyard grass, large crabgrass, radish, common purslane, redroot pigweed and false pimpernel were individually sowed in flower pots. After covering the seeds with soil, test compounds in such amounts as shown in Table 1 were individually applied to the soil. Thereafter, the test plants were grown in a greenhouse and, the herbicidal effects of the individual compounds were investigated to obtain the results as set forth in Table 1. Herbicidal effects were evaluated by the numerals ranging from 0 (not damaged) to 5 (completely killed). All the compounds were formulated into emulsifiable concentrates, and aqueous dilutions thereof were used.

Table 1

Herbicidal effects by pre-emergence application.

| Name of compound | Amount of active ingredient (g./are) | Barnyard grass | Large crabgrass | Radish | Common purslane | Redroot pigweed | False pimpernel |
|---|---|---|---|---|---|---|---|
| (1) | 50 | 5 | 5 | 1 | 5 | 5 | 5 |
| | 25 | 5 | 5 | 0 | 5 | 5 | 5 |
| | 12.5 | 4 | 4 | 0 | 4 | 5 | 4 |
| | 6 | 4 | 4 | 0 | 3 | 4 | 4 |
| (2) | 50 | 5 | 5 | 0 | 5 | 5 | 5 |
| | 25 | 5 | 5 | 0 | 5 | 5 | 5 |
| | 12.5 | 4 | 5 | 0 | 4 | 5 | 5 |

Table 1-continued

Herbicidal effects by pre-emergence application.

| Name of compound | Amount of active ingredient (g./are) | Barnyard grass | Large crabgrass | Radish | Common purslane | Redroot pigweed | False pimpernel |
|---|---|---|---|---|---|---|---|
| | 6 | 4 | 4 | 0 | 4 | 4 | 4 |
| | 50 | 5 | 5 | 0 | 5 | 5 | 5 |
| | 25 | 5 | 5 | 0 | 5 | 5 | 5 |
| (3) | 12.5 | 4 | 5 | 0 | 4 | 5 | 4 |
| | 6 | 4 | 4 | 0 | 3 | 4 | 4 |
| | 50 | 5 | 5 | 0 | 5 | 5 | 5 |
| | 25 | 5 | 5 | 0 | 5 | 5 | 5 |
| (4) | 12.5 | 5 | 5 | 0 | 4 | 5 | 4 |
| | 6 | 4 | 4 | 0 | 4 | 4 | 4 |
| | 50 | 5 | 5 | 0 | 5 | 5 | 5 |
| (5) | 25 | 5 | 5 | 0 | 5 | 5 | 5 |
| | 12.5 | 5 | 5 | 0 | 4 | 5 | 5 |
| | 6 | 4 | 5 | 0 | 4 | 4 | 4 |
| | 50 | 5 | 5 | 0 | 5 | 5 | 5 |
| (6) | 25 | 5 | 5 | 0 | 5 | 5 | 5 |
| | 12.5 | 5 | 5 | 0 | 5 | 5 | 5 |
| | 6 | 4 | 4 | 0 | 4 | 4 | 4 |
| | 50 | 5 | 5 | 0 | 5 | 5 | 5 |
| (7) | 25 | 5 | 5 | 0 | 5 | 5 | 5 |
| | 12.5 | 4 | 5 | 0 | 4 | 4 | 5 |
| | 6 | 3 | 4 | 0 | 4 | 4 | 4 |
| | 50 | 5 | 5 | 0 | 5 | 5 | 5 |
| | 25 | 5 | 5 | 0 | 5 | 5 | 5 |
| (8) | 12.5 | 4 | 5 | 0 | 4 | 5 | 4 |
| | 6 | 4 | 4 | 0 | 3 | 4 | 4 |
| (iso)C$_3$H$_7$NH–P(=S)(OCH$_3$)–O–C$_6$H$_3$Cl$_2$ | 50 | 5 | 4 | 1 | 2 | 2 | 2 |
| | 25 | 3 | 2 | 0 | 0 | 1 | 0 |
| | 12.5 | 1 | 0 | 0 | 0 | 0 | 0 |
| | 6 | 0 | 0 | 0 | 0 | 0 | 0 |
| U.S.P. 3,074,790 (iso)C$_3$H$_7$NH–P(=S)(OCH$_3$)–O–C$_6$H$_4$NO$_2$ | 50 | 5 | 5 | 2 | 5 | 4 | 4 |
| | 25 | 3 | 4 | 0 | 4 | 3 | 3 |
| | 12.5 | 2 | 2 | 0 | 2 | 0 | 1 |
| | 6 | 0 | 1 | 0 | 0 | 0 | 0 |

Belgian Pat. 745,633

TEST EXAMPLE 2

Wagner pots of 14 cm. in diameter, which had been packed individually with 1.5 kg. of paddy field soil, were brought into the state of paddy fields. To the pots were transplanted rice seedings at the 3-leaves stage. Further, seeds of barnyard grass were sowed in the pots and, after covering with soil, the test plants were grown in a greenhouse. On the second day after the sowing given amounts of test compounds were individually applied to the soil under water lodged conditions. Broad-leaved weeds germinated were monochoria, false pimpernel and toothcup. After 25 days the herbicidal effects and the phytotoxicity thereof to the rice seedings were investigated to obtain the results as set forth in Table 2. The herbicidal effects and the phytotoxicity were evaluated by numerals ranging from 0 (not damaged) to 5 (completely killed).

Table 2

Herbicidal effects in application under water conditions.

| Name of compound | Amount of active ingredient (gram/are) | Barnyard grass | Herbicidal effects on Broad-leaved weeds | Phytotoxicity on rice |
|---|---|---|---|---|
| (1) | 50 | 5 | 5 | 0 |
| | 25 | 5 | 5 | 0 |
| | 12.5 | 4 | 4 | 0 |
| (2) | 50 | 5 | 5 | 0 |
| | 25 | 5 | 5 | 0 |
| | 12.5 | 4 | 5 | 0 |
| (3) | 50 | 5 | 5 | 0 |
| | 25 | 5 | 5 | 0 |
| | 12.5 | 5 | 4 | 0 |
| (4) | 50 | 5 | 5 | 0 |
| | 25 | 5 | 5 | 0 |
| | 12.5 | 5 | 5 | 0 |
| (5) | 50 | 5 | 5 | 0 |
| | 25 | 5 | 5 | 0 |
| | 12.5 | 5 | 5 | 0 |
| (6) | 50 | 5 | 5 | 0 |
| | 25 | 5 | 5 | 0 |

Table 2-continued

| Name of compound | Amount of active ingredient (gram/are) | Barn-yard grass | Herbicidal effects on Broad-leaved weeds | Phyto-toxicity on rice |
|---|---|---|---|---|
| (7) | 12.5 | 4 | 5 | 0 |
|  | 50 | 5 | 5 | 0 |
|  | 25 | 5 | 5 | 0 |
|  | 12.5 | 4 | 4 | 0 |
| (8) | 50 | 5 | 5 | 0 |
|  | 25 | 5 | 5 | 0 |
|  | 12.5 | 4 | 4 | 0 |
| (iso)C₃H₇NH\P(=S)(OCH₃)O–C₆H₃Cl₂ U.S.P. 3,074,790 | 50 | 4 | 2 | 1 |
|  | 25 | 2 | 0 | 0 |
|  | 12.5 | 0 | 0 | 0 |
| (iso)C₃H₇NH\P(=S)(OCH₃)O–C₆H₄NO₂ Belgian Pat. 745633 | 50 | 5 | 4 | 0 |
|  | 25 | 3 | 2 | 0 |
|  | 12.5 | 1 | 0 | 0 |

What we claim is:

1. A compound of the formula

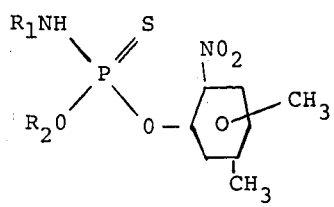

wherein $R_1$ is sec-butyl and $R_2$ is methyl or ethyl.

2. A compound of claim 1, wherein $R_2$ is methyl.
3. A compound of claim 1, wherein $R_2$ is ethyl.
4. A compound of claim 1, namely

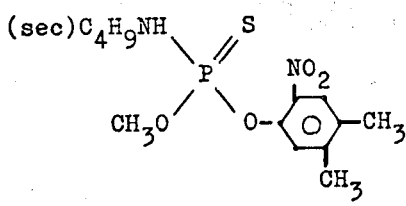

5. A compound of claim 1, namely

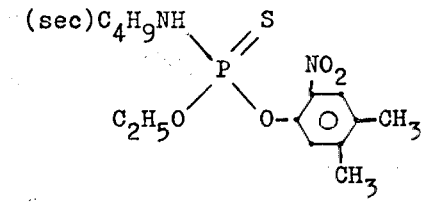

6. A compound of claim 1, namely

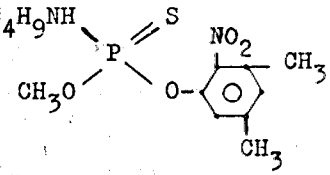

7. A compound of claim 1, namely

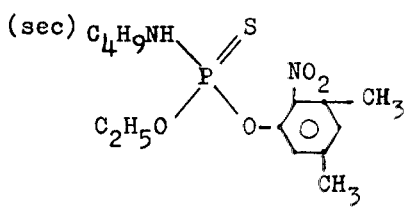

* * * * *